United States Patent

Van Driel

[11] Patent Number: 5,904,676
[45] Date of Patent: May 18, 1999

[54] GASKETLESS SEAL FOR ROTATABLE BLOOD RESERVOIR CONNECTOR

[75] Inventor: Michael R. Van Driel, Fountain Valley, Calif.

[73] Assignee: Medtronic, Inc., Minneapolis, Minn.

[21] Appl. No.: 08/728,873

[22] Filed: Oct. 10, 1996

[51] Int. Cl.⁶ .................................................. A61B 19/00
[52] U.S. Cl. .................... 604/403; 422/46; 210/321.79
[58] Field of Search .................. 604/403, 404, 604/405, 406, 407; 220/3.2, 327; 422/44–46; 210/321.2, 321.4; 128/DIG. 3

[56] References Cited

U.S. PATENT DOCUMENTS

| | | | |
|---|---|---|---|
| 4,782,841 | 11/1988 | Lopez | 128/164 |
| 4,876,066 | 10/1989 | Bringham et al. | 422/46 |
| 5,066,287 | 11/1991 | Ryan | 604/240 |
| 5,403,273 | 4/1995 | Lindsay . | |
| 5,470,324 | 11/1995 | Cook et al. . | |

OTHER PUBLICATIONS

Sorin Biomedical Monolyth Brochure, Mar. 1995.

*Primary Examiner*—Robert A. Clarke
*Assistant Examiner*—Ki Yong O
*Attorney, Agent, or Firm*—Harry G. Weissenberger

[57] ABSTRACT

A gasketless seal is formed between a flow tube in a venous reservoir and a rotatable connector telescoped into it, by forming on the connector one or more annular ribs of slightly larger diameter than the inner diameter. When the connector is inserted into the flow tube, the rib is partially crushed against the inner wall of the flow tube and forms a tight, rotatable seal with it.

4 Claims, 3 Drawing Sheets

GASKETLESS SEAL FOR ROTATABLE BLOOD RESERVOIR CONNECTOR

FIELD OF THE INVENTION

This invention relates to a rotatable venous inlet connector in a hardshell venous reservoir, and more particularly to a gasketless double seal which is formed in situ by the insertion of the connector into the venous flow tube.

BACKGROUND OF THE INVENTION

Hardshell venous reservoirs are used in extracorporeal bypass circuits during cardiac surgery to store the extra volume of blood produced in the patient's circulatory system by the dilution of the patient's blood in preparation for open heart surgery. The reservoir also serves as a buffer to absorb variations between the volume of blood exiting the patient through a venous tap and cardiotomy suction, and the volume of blood drawn by the pump of the heart-lung machine for oxygenation and return to the patient.

Conventionally, venous blood is introduced into the reservoir through a venous inlet connector which is fitted into the cover of the top entry reservoir, and which can be rotated about an axis perpendicular to the plane of the cover. Blood from the venous inlet connector is discharged into a venous flow tube which fits over the bottom end of the connector and conveys the blood to an appropriate venous defoamer chamber in the reservoir.

In order to minimize foaming and risk of contamination of the venous blood, it is essential that air be prevented from entering the blood stream at the interface of the flow tube and the connector. Prior art constructions have addressed that problem by providing one or more 0-ring seals between the connector and the flow tube. The prior art construction was, however, not completely satisfactory because, firstly, biocompatible silicone 0-rings are not inexpensive; because, secondly, their relatively high friction coefficient makes it harder than necessary to rotate the connectors; and because, thirdly, the patient's blood should be exposed to as few different materials as possible during surgery.

A need consequently existed in the prior art for an inexpensive, airtight rotatable joint between the telescoping connector and flow tube.

SUMMARY OF THE INVENTION

The present invention fills the above-described need and allows the perfusionist to easily rotate the venous inlet connector into any desired position while maintaining the integrity of the venous line seal against entry of deleterious microair without the use of 0-rings, by forming the connector with a plurality of annular ribs so dimensioned that they crush and seal against the interior of the flow tube when inserted into it.

DESCRIPTION OF THE PREFERRED EMBODIMENT

Figure 1:
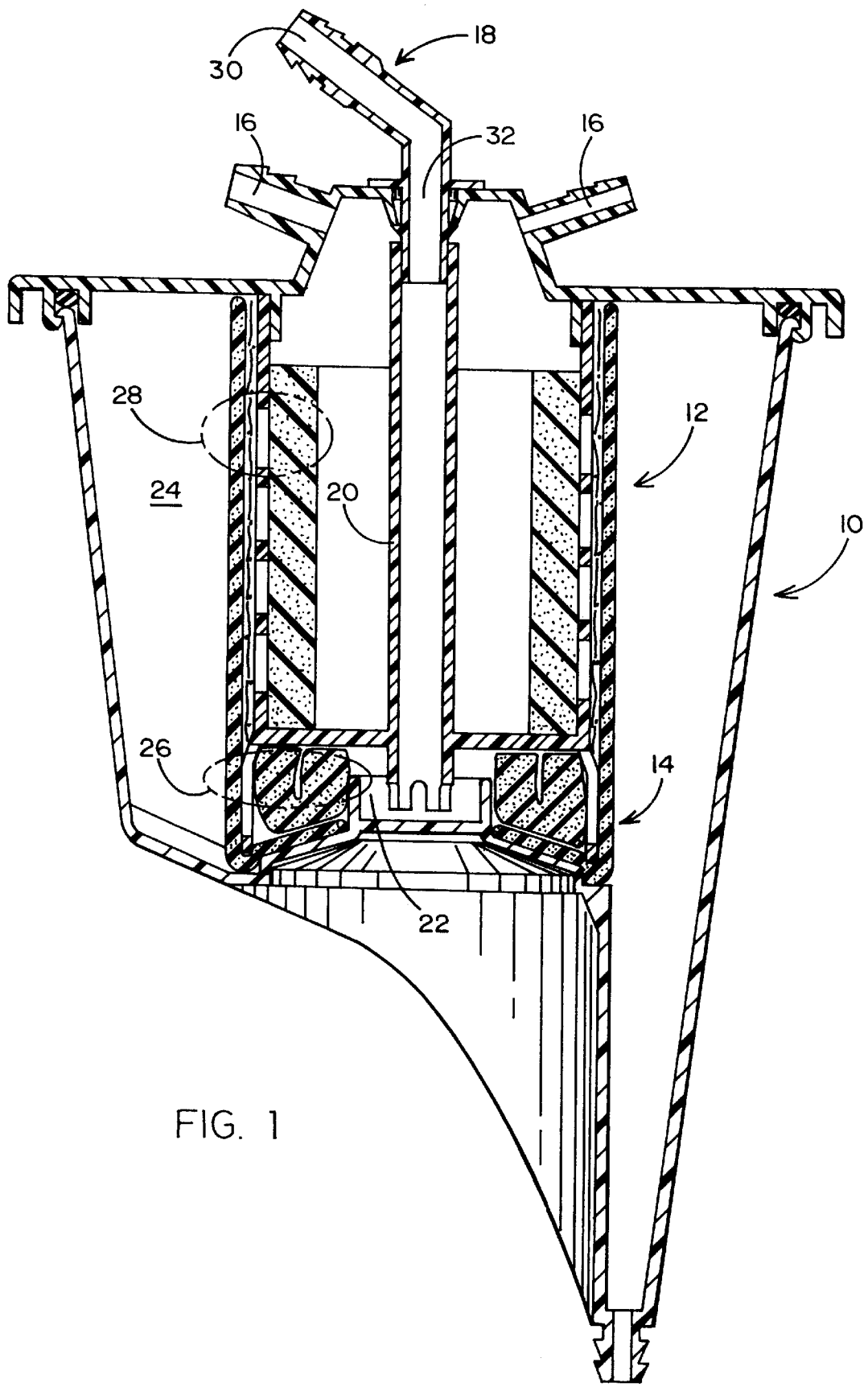
FIG. 1 is a vertical section of a hardshell venous reservoir using the invention.

FIG. 1 is a vertical axial section of a typical hardshell venous reservoir 10 containing a cardiotomy filter/defoamer 12 and a venous microair defoamer 14. While cardiotomy blood is introduced into the filter/defoamer 12 through appropriate inlet connectors 16, venous blood is conveyed through the venous inlet connector 18 into an axially extended flow tube 20 and down into the venous chamber 22. The clean defoamed cardiotomy and venous blood enter the body 24 of the reservoir 10 through separate defoamers or filter/defoamers 26, 28.

The venous inlet connector 18 includes an angled connecting section 30 to which the inlet line from the patient's vena cava can be attached, and an axial fitting section 32 which fits into the flow tube 20. Formed around the fitting section 32 (FIGS. 2a–c) are two annular ribs 34, 36. The rib 36 is slightly smaller in diameter than the rib 34, and the spacing between the ribs 34, 36 is equal to the distance of the shoulder 38 from the top of the flow tube 20, both for a purpose hereafter described.

Figure 2B:
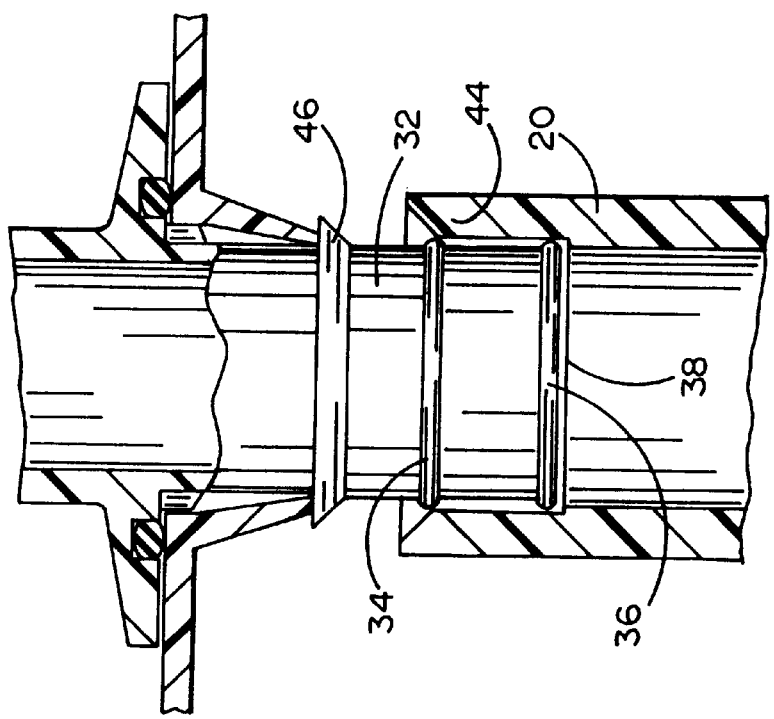
FIGS. 2a–c are detail vertical sections of the connector and flow tube illustrating successive steps in their assembly.
Figure 2A:
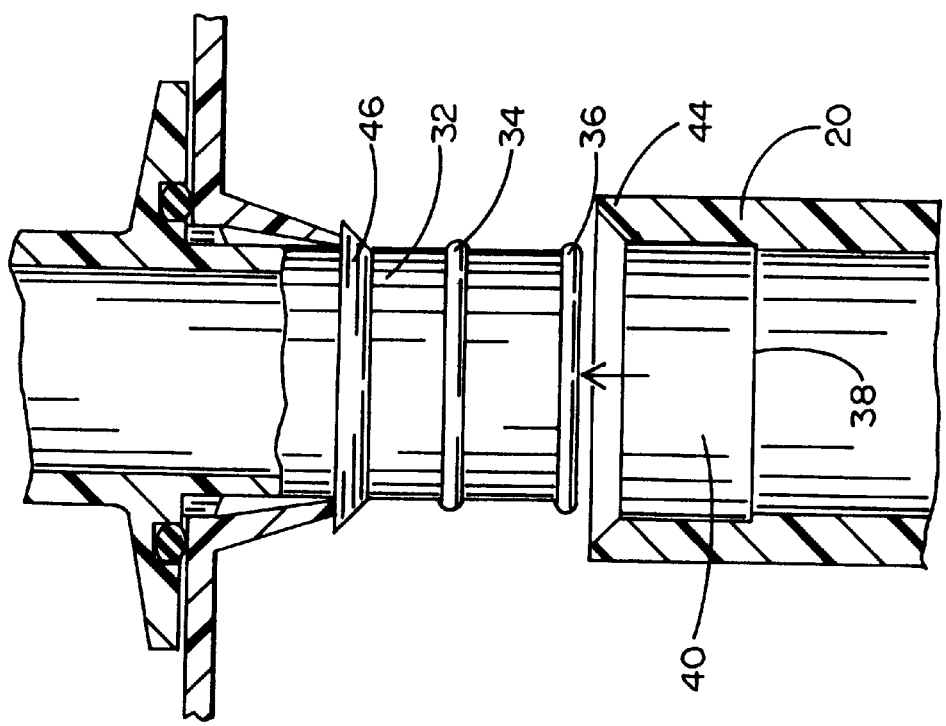
Figure 2C:
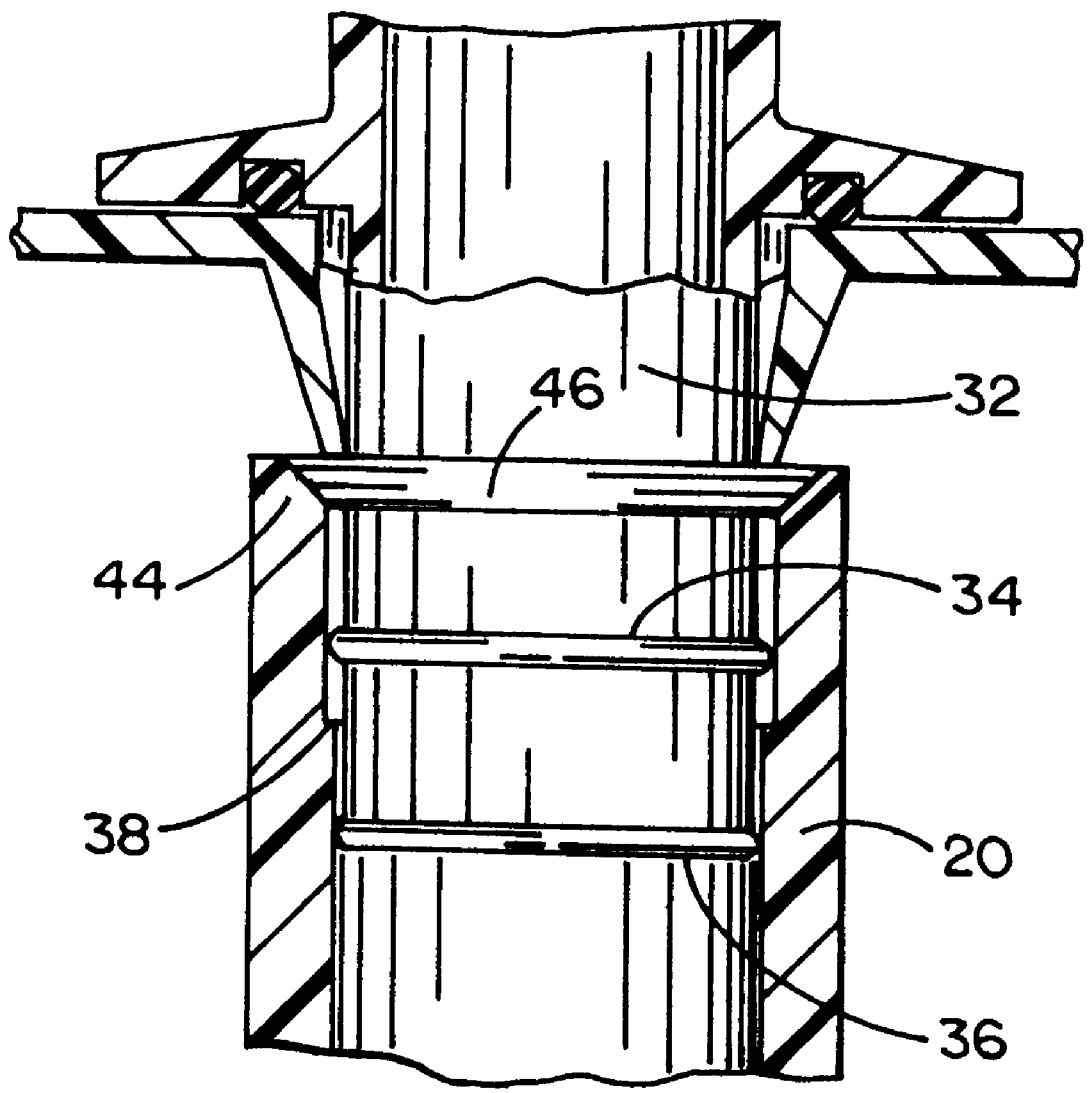

In a preferred embodiment, the connector 18 and the flow tube 20 may both be formed from a hard plastic such as polycarbonate or any thermoplastic material. The ribs 34, 36 may be semicircular in cross section. FIGS. 2a–c illustrate what happens when the connector 18 and the flow tube 20 are mated. First, the lower portion of the fitting section 32 fits through the upper portion 40 of flow tube 20 with sufficient clearance to prevent rib 36 from touching the tube 20 (FIG. 2a). Eventually, because the distance between them is equal to the length of the upper portion 40, the ribs 34, 36 simultaneously touch the rim 44 of the flow tube 20 and the shoulder 38 (FIG. 2b). Finally, further insertion of the connector 18 into the flow tube 20 crushes the ribs 34, 36 against the walls of flow tube 20 and seats them firmly against the walls of the flow tube 20 when the flange 46 of the connector 18 seats against the rim 44 of the flow tube 20 (FIG. 2c).

The above-described construction permits the forming of the sealing elements 34, 36 integrally with the rotatable connector 18, thus eliminating the failure risk factors associated with the provision and installation of an additional part. It also provides a better fit between the connector 18 and flow tube 20, and facilitates the rotation of connector 18. Although tests have shown that a tight seal can be achieved with a single rib 34, the use of a double seal by ribs 34 and 36 provides an additional level of safety.

It is understood that the exemplary gasketless seal for rotatable blood reservoir connectors described herein and shown in the drawings represently only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

I claim:

1. A hard-shell blood reservoir for heart-lung machines, comprising:

a) a housing;

b) a cover for said housing;

c) a substantially cylindrical filter extending in said housing downwardly from said cover;

d) a substantially cylindrical flow tube extending longitudinally of said filter in said housing;

e) a substantially cylindrical connector telescopable into said flow tube and rotatable with respect thereto;

f) said flow tube being formed of plastic, with an inner wall having an inner diameter;

g) said connector being also formed of plastic and having an outer diameter smaller than said inner diameter to allow telescoping of a part of said connector into said flow tube;

h) a ring-shaped annular tip formed on said part, said rib having a maximum diameter slightly larger than said inner diameter;

i) said rib and wall cooperating to form a gasketless sealed fitting by being so dimensioned that, upon telescoping insertion of said part into said flow tube, said rib is annularly crushed against said wall to form a rotatable seal between said part and said flow tube.

2. The fitting of claim 1, in which said flow tube has a portion of larger inner diameter and a portion of smaller inner diameter, said larger inner diameter portion extending a predetermined distance from the rim of said flow tube, and said part has formed thereon a rib of slightly larger maximum diameter than said larger inner diameter and a rib of slightly larger maximum diameter than said smaller inner diameter.

3. The fitting of claim 2, in which said ribs are spaced from each other by said predetermined distance.

4. The fitting of claim 2, in which said part has a flange formed thereon, said flange being adapted to engage said rim of said flow tube to limit telescoping movement of said connector with respect to said flow tube.

* * * * *